United States Patent [19]
Shinohara et al.

[11] Patent Number: 4,514,560
[45] Date of Patent: Apr. 30, 1985

[54] AGGREGATING POLYSACCHARIDE DERIVED FROM AUREOBACIDIUM

[76] Inventors: Satoru Shinohara, No. 8-14, Takasago-cho, Hyuga-shi, Miyazaki-ken; Noboru Fujii, No. 37 Haramachi 1-chome; Kiyohisa Imada, No. 41-5, Otsukadainishi 3-chome, both of Miyazaki-shi, Miyazaki-ken; Genichi Kadota, No. 6276-83, Tomitaka, Hyuga-shi, Miyazaki-ken; Hideo Ueno, No. 608, Zaikoji, Hyuga-shi, Miyazaki-ken, all of Japan

[21] Appl. No.: 353,968

[22] Filed: Mar. 2, 1982

[30] Foreign Application Priority Data

Mar. 11, 1981 [JP] Japan ................................ 56-35001

[51] Int. Cl.$^3$ ............................................. C12P 19/04
[52] U.S. Cl. ........................................ 536/1.1; 127/29; 426/573; 426/658; 435/101; 435/171; 435/911; 536/117; 536/127
[58] Field of Search ................ 435/101, 171, 911; 127/29; 536/1.1, 117, 127; 426/573, 658

[56] References Cited

U.S. PATENT DOCUMENTS 4,258,132  3/1981  Shinohara ......................... 435/101

OTHER PUBLICATIONS

Chemical Abstracts, 88:71282w (1978).
Chemical Abstracts, 91:73150n (1979).
Chemical Abstracts, 92:160255q (1980).
Chemical Abstracts, 93:200694m (1980).

Primary Examiner—Sidney Marantz
Attorney, Agent, or Firm—Armstrong, Nikaido, Marmelstein & Kubovcik

[57] ABSTRACT

A polysaccharide contains D-glucose as main constitutive sugar according to gas chromatography carried out through methylation in accordance with the Hakomori's method; and hydrolysis and to paper chromatography carried out through acid hydrolysis shows $G^1 \rightarrow : \rightarrow ^3G^1 \rightarrow : \rightarrow ^3G_6^1 \rightarrow = 0.38-0.43 : 0.14-0.24 : 0.38-0.43$ in gas chromatographic mass spectrometry (GC-MS method); has the signal of $C_1$ at 103 ppm as measured from a $^{13}C$-nuclear magnetic resonance spectrum; shows characteristic absorption at 1720 cm$^{-1}$–1760 cm$^{-1}$ and 890 cm$^{-1}$ in an infrared absorption spectrum; has number average molecular weight between 50,000 and 500,000 as measured by the osmotic pressure; has a specific rotation $[\alpha]_D^{25}$ between +20 and +70; consists 42.0 to 45.0% of carbon, 5.7 to 6.7% of hydrogen, 0 to 1.0% of nitrogen, 0.2 to 0.8% of ash content and the rest of oxygen according to the results of an elementary analysis; contains 4.0 to 6.0% of phosphoric acid in total as measured by a fluorescent X-ray analysis, the Allen's improved method, and the Deniges-Atkins method after carbonic acid melting; shows a color reaction of saccharides through an α-naphthol-sulfuric acid reaction, an indole-sulfuric acid reaction and a phenol-sulfuric acid reaction; is negative in a ninhydrin reaction, a carbazole-sulfuric acid reaction and an Elson-Morgan's reaction; is soluble in dimethyl sulfoxide (DMSO); swells well, though not readily soluble in water; and is insoluble in ethanol, pyridine, chloroform and other organic solvents.

7 Claims, 13 Drawing Figures

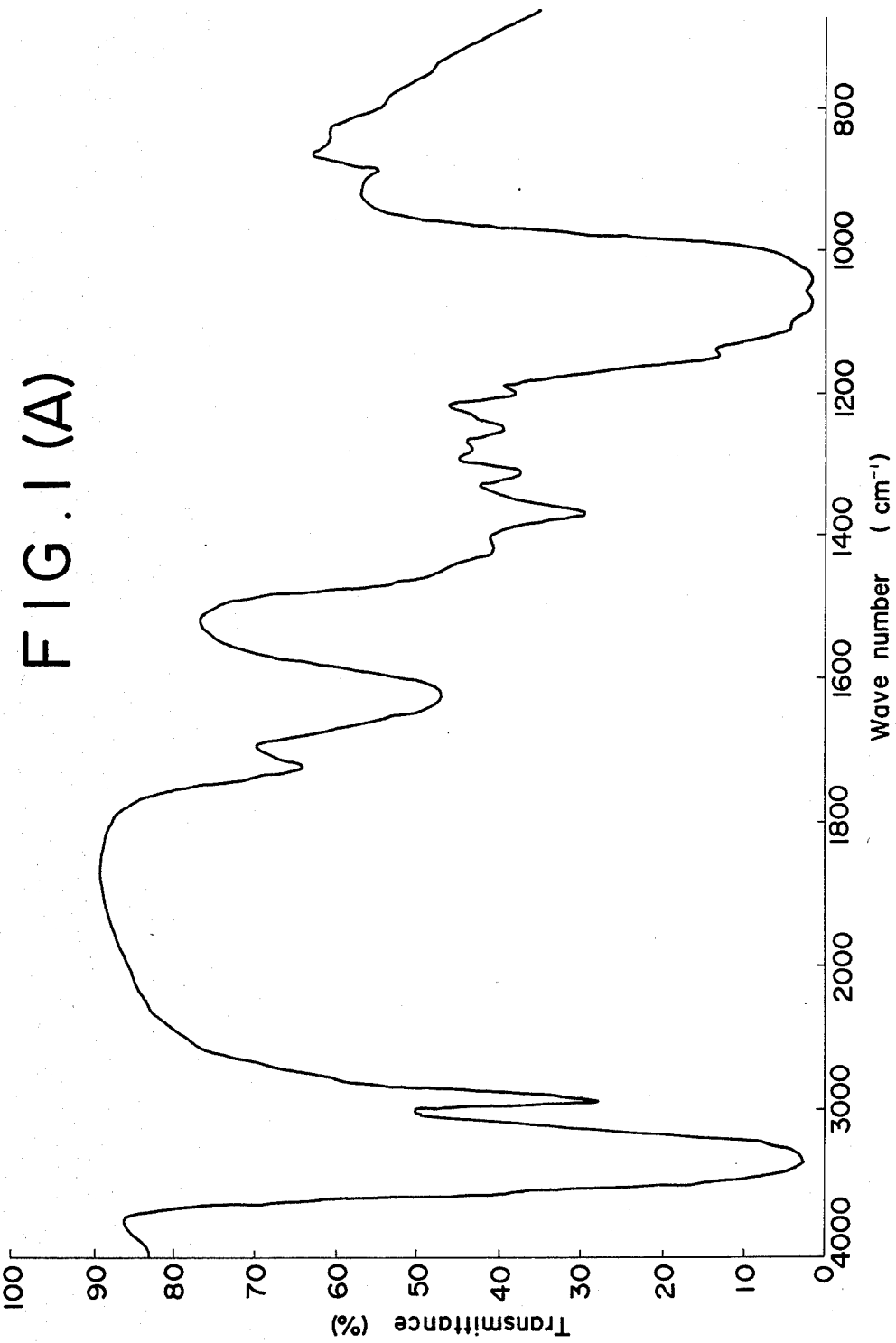

AGGREGATING POLYSACCHARIDE DERIVED FROM AUREOBACIDIUM

BACKGROUND OF THE INVENTION

1. Field of the Invention

This invention relates to a novel polysaccharide having glucose as the main constitutive sugar thereof, the bonding mode thereof being β-linkage the principal chain being of β-1,3 linkage the non-reducing end-group thereof branching at β-1,6 linkage 38.0 to 43.0% thereof being the non-reducing end-group, and further containing 4.0 to 6.0% of phosphoric acid and more particularly to an extracellar, cell wall polysaccharide produced by an Fungi Imperfecti (deposited at Biseibutsu Kogyo Gijutsu Kenkyusho, Deposite No. 4257) belonging to the genus of aureobacidium in the family of black fungi.

2. Description of the Prior Art

In the course of a research for polysaccharides contained in raw sugar, the present inventors isolated a strain belonging to the genus of aureobacidium having strong kaolin aggregation activity. They compared the isolated strain with scores of different kinds of known strains belonging to the genus of aureobacidium or that of pullularia to find that the isolated fungus was strongly productive of kaolin agglutination activity. They established a method for culturing the isolated fungus. Further, they conducted studies for utilization of this substance as agglutinating agent. Eventually, a method for the manufacture of the agglutinating agent and a method for the utilization of the same were developed as disclosed in Japanese Patent Application No. 121687/1977 and No. 097664/1978. A food modifying agent was further developed as disclosed in Japanese Patent Application No. 007816/1979.

The agglutinating agent prepared by using the above stated isolated fungus (deposited at Biseibutsu Kogyo Gijutsu Kenkyusho, Deposite No. 4257 and at American Type Culture Collection, Deposit No. 20524, i.e., ATCC No. 20524) has come to be manufactured on an industrial production scale for practical use. The present inventors gave attention to the physicochemical properties of this actively agglutinating substance, such as high viscosity, nonadhesiveness, unique agglutination with aluminum ion, jellification of an ethanol solution and formation of an insoluble matter by acid hydrolysis. They isolated the effective component of the actively agglutinating substance and conducted analysis on the physical and chemical structure thereof. It was thus found that this effective component was a polysaccharide. This was a novel polysaccharide which had glucose as the main constitutive sugar thereof, the bonding mode thereof was such that the principal chain was β-1,3 and 38.0 to 43.0% thereof was a non-reducing end-group branching at β-1,6. The polysaccharide further contained 4.0 to 6.0% of phosphoric acid group and liberated an acid matter when subjected to an alkali treatment. This finding has led to the present invention. In the meantime, polysaccharides of β-1,3 linkages has recently come to draw public attention as anti-tumor polysaccharides.

SUMMARY OF THE INVENTION

It is therefore a general object of the invention to provide a novel polysaccharide in which the main constitutive sugar is glucose; the bonding mode is β-bond and the principal chain is of β-1,3 linkages the non-reducing end-group thereof branches at β-1,6 bond; 38.0 to 43.0% thereof is the non-reducing end-group; and there is contained 4.0 to 6.0% of phosphoric acid.

The above and further objects, features and advantages of the invention will become apparent from the following detailed description thereof taken in connection with the accompanying drawings.

BRIEF DESCRIPTION OF THE DRAWINGS

FIG. 1(A) is a graph showing the infrared absorption spectrum of the invented polysaccharide.

DETAILED DESCRIPTION OF THE INVENTION

I. Examples of Manufacture and Purification of Polysaccharide of the Invention:

The liquid culture of the above stated fungus No. 4257 isolated by the present inventors or, more specifically, aerated cuture of the fungus under the conditions including 0.5 to 1.0% of a carbon source (sucrose); 0.1% of an N source; addition of some slight quantity of substance, such as a vitamin or an inorganic substance; pH 5.2 to 6.0; aeration arranged to be $\frac{1}{2}$ to $\frac{1}{3}$ of the volume of the culture medium; dissolved oxygen not exceeding 1.0 ppm; and temperature between 20° and 30° C. produces the invented polysaccharide within the culture medium. The culture medium presents an yellow color and is in a egg-white gel state. The concentration of the polysaccharide thus produced is about 0.3% and varies with physical restrictions imposed. It is, however, possible to increase the production concentration up to a value between 0.5 and 0.6% by some suitable arrangement of the composition of the culture medium.

Figure 12:
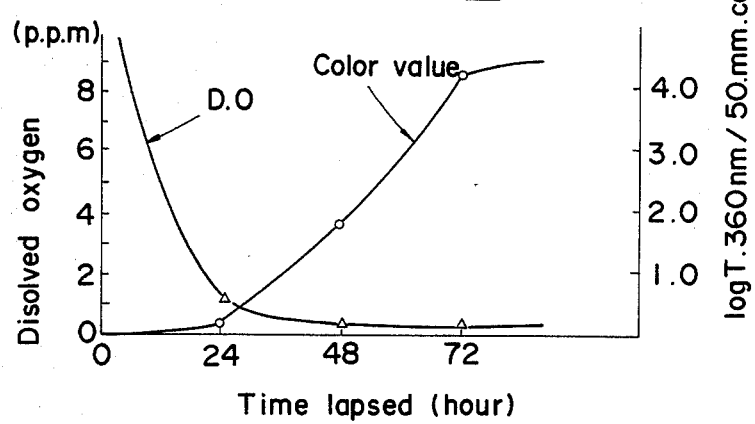
FIG. 12 is a graph showing agglutination brought about by the method of culturing the substance of the present invention.

To put it more specifically, in an example, the culture was carried out using a culture tank (manufactured by Takasugi Seisakusho) measuring 1 m³, a seed fungus culture tank (manufactured by Takasugi Seisakusho) measuring 50 liters, a dissolved oxygen meter, a pH meter and a thermometer. Measurement was carried out with automatic recording arrangement. The laying-in amount was 1 m³. The seed fungus quantity was 40 liters. The culture time was 48 hours. The composition of the culture medium included 0.5% of the carbon source; 0.1% of the N source and 0.1%–0.2% of slightly amounting substances such as vitamins and/or inorganic substances (for example 10 ppm of Mg, 30 ppm of P and 0.2% of vitamin C). The pH value was 5.2±0.2. The culture temperature was 25° C.±2° C. The rate of aeration was $\frac{1}{3}$ per min of the volume of the laying-in culture medium. The results of the culture were as shown in Table 1(A) below and in FIG. 12.

TABLE 1(A)

| Culture time lapsed (hr) | pH | Kaolin aggregative activity, ppm | Novel polysaccharide (insoluble in 50% ethanol), ppm | Viscosity CP/20° C., relative viscosity* | $Al^{+++}$ reaction |
| --- | --- | --- | --- | --- | --- |
| 0 | 5.2 | 0 |  | 0.1 |  |
| 24 | 5.1 | 1,000 | 1,160 | 4.5 | + |
| 48 | 5.0 | 3,000 | 2,600 | 22.4 | ++ |
| 72 | 4.8 | 3,300 | 3,240 | 32.2 | ++ |

Note
*Relative viscosity was obtained by an Oswald's viscometer.

The culture liquid had the polysaccharide of the present invention as the main constituent thereof. However, there were contained some fungus body, nonused reduced sugar (glucose), lipid and other insoluble matters therein.

PURIFICATION EXAMPLE 1

The above stated polysaccharide of the present invention was isolated and purified in a manner as shown in Table 2 below:

TABLE 2

Culture liquid after completion of the culture

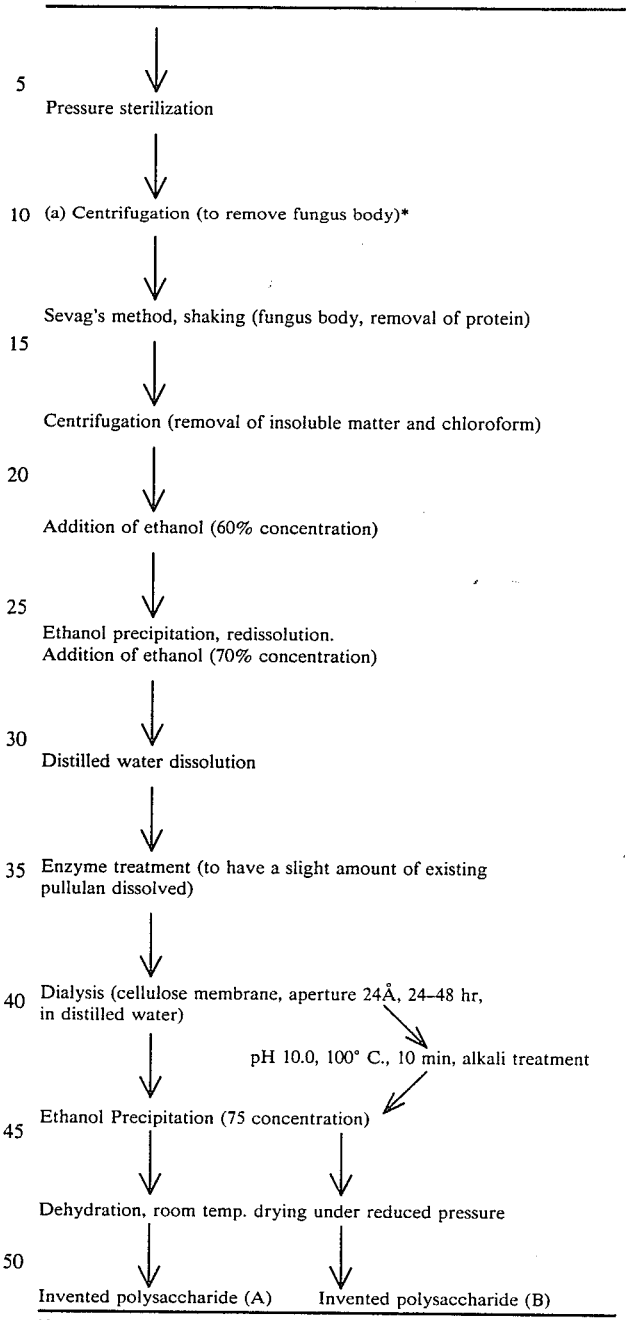

Note:
*For an aggregating agent and a food modifying agent, the product obtained at the step (a) was used.
(A): In a white fibrous state
(B): A white fibrous state (does not show absorption of 1720–1740 cm$^{-1}$ in infrared analysis)

Referring to Table 2 above, the centrifugation was carried out at a rate of 5,000 rpm for the purpose of removing the fungus body and insoluble solids. To have the fungus body, protein and lipid more completely removed, 10% of a chloroform-butanol mixture solution was added to the treatment liquid and the liquid was shaken (according to the Sevag's method). Then, the mixture is subjected to a centrifugation treatment (10,000 rpm-15 min) to remove the chloroform and insoluble matters. Lipid can be also removed by this. With this process of treatment repeated twice, the culture liquid became transparent with the fungus body completely removed therefrom. To this was added ethanol to make ethanol concentration 60%. The liquid was stirred. It showed a gel like state at an early stage and then came to show a fibrous state according as stirring further continues. Following this, the ethanol concentration was increased to 70% to physically effect dehydration. This causes complete removal of ethanol soluble lipid. Then, dissolution in distilled water gave a colorless, transparent liquid, which was somewhat whitely turbid. This seems to be attributable to the physical structure, i.e. the solubility, of the polysaccharide of the present invention. Further, since mixed presence of a slight amount of pullulan was also conceivable, a decomposing enzyme was allowed to act and dialysis was further carried out in distilled water. During the dialysis, in some cases, mixed presence of inorganic ion might render the polysaccharide of the invention insoluble. The dialysis liquid was alcohol precipitated (80% concentration) to isolate and purify the polysaccharide of the present invention. After dialysis, the pH value was adjusted to 10.0 with NaOH. Alkali treatment was then carried out at 100° C. for 10 min to obtain a polysaccharide which did not show any absorption at $1720 \text{ cm}^{-1}$–$1760 \text{ cm}^{-1}$ when subjected to an infrared analysis.

This substance possessed a physical property that did not permit purification thereof by ordinary gel filtration, physical filtration or ion exchange.

PURIFICATION EXAMPLE 2

Fifteen liters of the culture liquid obtained by the above stated example was sterilized at 110° C. over a period of 10 min and then was centrifugalized at 5,000 rpm. The liquid thus treated was divided and put in a one liter separating funnel. To this was added 100 ml of a chloroform-butanol mixture solution. Extraction was effected with shaking at room temperature and an extract thus obtained was subjected to centrifugation at 10,000 rpm for 15 min to separate chloroform and the fungus body from each other. The same process was repeated once more. To the treated liquid was gradually added about 20 liters of ethanol with stirring. The liquid was dissolved in distilled water (0.3% concentration). The pH value thereof was adjusted to 5.2. After that, a crystalline pullulanase (manufactured by Hayashibara Co.) was added with stirring carried out at 30° C. over a period of 24 hours. Dialysis was carried out with a cellulose membrane. In the case of city water, there would be produced an insoluble matter. After completion of the dialysis, 40 liters of ethanol was added. The liquid was left intact for a period of 24 hours. An insoluble matter was then separated and dried at room temperature under reduced pressure to obtain the polysaccharide of the present invention.

TABLE 3

| Sample: Culture liquid, 15 liters→ | Novel polysaccharide (solid matter), 44 g |
|---|---|

The polysaccharide of the invention thus obtained was in a colorless, odorless white fibrous state.

II. Physical and Chemical Properties of the Invented Substance (a) Elementary Analysis Values:

The invented substance was subjected to an elementary analysis, which was carried out with an apparatus called CHN-CORDER Model MF 2, manufactured by Yanagimoto Seisakusho. The results of the elementary analysis: 42.0 to 45.0% (43%) of carbon, 5.7 to 6.7% (6.4%) of hydrogen, 0.2 to 0.8% (0.6%) of ash content and 0 to 1.0% (0.8%) of nitrogen. The rest was oxygen.

(b) Color Reaction:

The substance was subjected to various color reaction tests in a state of being dissolved in water. Table 4 shows the results of tests.

TABLE 4

| Color reaction | Color | Results |
|---|---|---|
| Molish reaction | | Sugar |
| α-naphthol-sulfuric acid reaction | Purple | " |
| Indole-sulfuric acid reaction | Brown | " |
| Phenol-sulfuric acid reaction | Yellow | " |
| Carbazole-sulfuric acid reaction | (Quantitative) | No uronic acid contained |
| Elson-Morgan's reaction | (Quantitative) | No amino acid contained |
| Ninhydrin reaction | — | No amino acid contained |

The results of the qualitative and quantitative reaction tests shown in the above table indicate that the substance tested was a glucide and did not contain uronic acid nor amino acid.

(c) pH:

The pH value of the substance was measured with a pH meter, "HM 5A" manufactured by Toa Denpa, by dissolving 0.1 g of the substance in 100 ml of distilled water. The measured pH value was 6.5 to 6.6.

(d) Specific Rotation:

The optical rotatory power of the substance was measured with a self polarimeter, JASCO J-20A, by preparing the substance into a 0.2% aqueous solution thereof. The specific rotation $[\alpha]_D^{25}$ was obtained from the measured optical rotation. The value thus obtained was within the range of $+20°$–$70°$ (40°).

(e) Molecular Weight:

The number average molecular weight of the substance was measured with an osmometer (cell) of the Zimm-Myerson type using a cellophane semipermeable membrane. The measured number average molecular weight thus obtained was between 100,000 and 500,000 (373,000). Further, the limiting viscosity of the aqueous solution of it, at 25° C., was $[\eta]=1.0$ to 3.5 (2.40).

(f) Solubility:

While this substance can be swelled very well by water, a slight amount of mixed presence of impurities often coagulates the substance. Such coagulating impurities include ethanol, a sulfuric acid band, a basic polyelectrolyte, etc. Although the substance is insoluble in chloroform, benzene, hexane, pyridine, etc., the substance is swelled well by ethanol which contains water. However, an insoluble gel comes to precipitate at ethanol concentration exceeding 70%.

A nearly homogeneous gel can be obtained with the substance allowed to be swelled by a volume of water 10 to 100 times as much as that of the substance. Hereinafter this homogeneous gel will be called the aqueous solution of the substance.

Figure 1B:
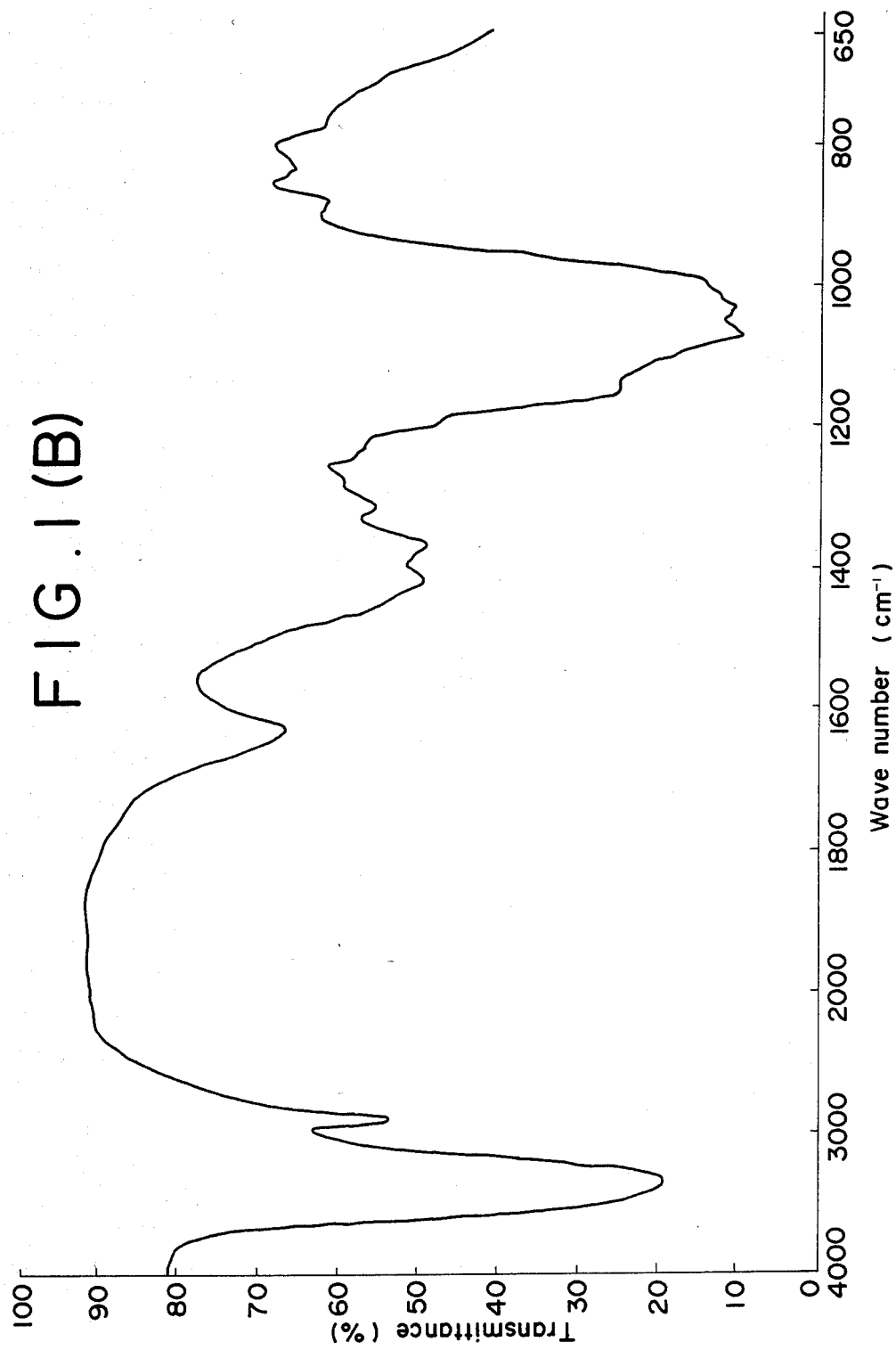
FIG. 1(B) is a graph showing the infrared absorption spectrum of the invented polysaccharide which has been alkali treated.

(g) Infrared Absorption Spectrum:

The infrared absorption spectrum of a filmy sample or a sample prepared by the KBr tablet method by drying up the aqueous solution of the substance is as shown in FIG. 1(A). With the substance alkali treated, the infrared absorption spectrum becomes as shown in FIG. 1(B) and shows a difference resulting from the treatment. As clearly shown, there are absorptions at about 3600 to 3100 cm$^{-1}$, 2950 to 2920 cm$^1$, 1760 to 1720 cm$^{-1}$, 1600 to 1680 cm$^{-1}$, 1400 to 1480 cm$^{-1}$, 1340 to 1390 cm$^1$, 1320 cm$^{-1}$, 1200 to 1000 cm$^{-1}$ and 890 cm$^{-1}$. Further, the measurement was carried out with a product of Nippon Bunkosha called Model DS-701.

Referring to FIG. 1, the broad absorption in the area of 3600-3200 cm$^{-1}$ is believed to be attributable to OH which is hydrogen bonded to various degrees. This particular absorption either decreases or disappears when the hydroxyl group in the glucide part of the sample is —o— methylated. Further, another broad absorption in the area of 1200-1000 cm$^{-1}$ is believed to be attributable to the asymmetric stretching vibration of the C—O—C bond of a pyranose ring in the glucide part. The absorption at 1720-1760 cm$^1$ is believed to indicate the C=O stretching vibration of the ester group and the nonionic property of —COOH. Another absorption at 890 cm$^{-1}$ is believed to indicate the β-anomer of the sugar. The absorption of 1720-1760 cm$^{-1}$ is caused to disappear by alkali treatment while the absorptions of 1720-1760 cm$^{-1}$ and 1250-1280 cm$^{-1}$ are caused to disappear by methylation. Further, the absorption of 1760-1720 cm$^{-1}$ peculiar to the carbonyl group C=O seems to be attributable to the ester bond of an organic acid with the sugar part or to the ketal bond of the organic acid in the case of an acid having a hydroxyl group besides a carboxyl group.

III. Physical Properties:

(a) Properties in Alcohol Aqueous Solution:

The aqueous solution (0.1%) of the substance is highly viscous but does not show any tackiness and adhesiveness. It presents a raw eggwhite like appearance. When its concentration in an aqueous solution becomes 1%, it comes to show a gel like appearance and is hardly soluble in water. With ethyl alcohol added to the 0.1% aqueous solution of the substance, the viscosity of the aqueous solution increases according as the concentration of the alcohol increases and thus comes to show a jelly like appearance. This feature of the substance is inferable either from the non-reducing end-group or from the branching bridge structure thereof. Because: The non-reducing end-group in this substance amounts to as much as 38 to 43%, which is very high content compared with other high molecular polysaccharides.

(b) Measurement of Viscosity of the Substance in Water-Alcohol Mixture System:

The substance was purified and powdered. The powdered substance was dissolved in distilled water to a concentration of 0.5%. Then, concentration of the substance in water-and-alcohol mixture systems was adjusted as shown in Table 5. The viscosity of each system was measured with a B type rotation viscometer with through stirring. The results of the measurement were as shown in FIG. 2.

Figure 2:
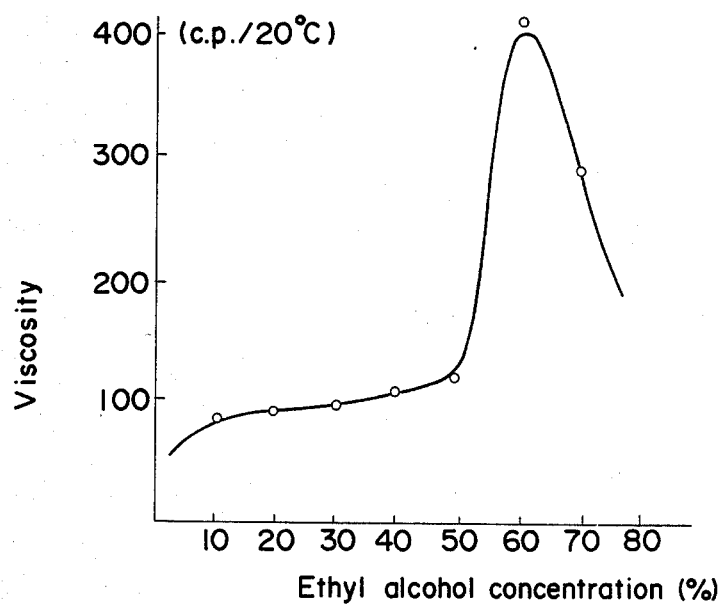
FIG. 2 is a graph showing the viscosity of the invented polysaccharide in a water-alcohol mixture system.

As shown in FIG. 2, the viscosity reaches a maximum value at an alcohol concentration of 60%. The maximum value is about 5 times as much as the viscosity value obtained without the addition of alcohol. In other words, the maximum viscosity of the 0.1% aqueous solution became 410 (C.P./20° C.) and the solution was jellified. The apparent properties of this jelly entirely differs from a well known jelly prepared by mixing pectic acid with sugar. The jelly of the present substance is soft, has no tackiness and is highly stretchable. These physical properties suggest that the polysaccharide of the present invention is useful as foundation base of a cosmetic or for jellied food containing ethanol and for other various processing materials.

TABLE 5

| Concentration of the novel polysaccharide: | 0.1% | 0.1% | 0.1% | 0.1% | 0.1% | 0.1% | 0.1% | 0.1% |
|---|---|---|---|---|---|---|---|---|
| Solvent - | | | | | | | | |
| Water: | 90 | 80 | 70 | 60 | 50 | 40 | 30 | 20 |
| Ethanol: | 10 | 20 | 30 | 40 | 50 | 60 | 70 | 80 |
| C.P./20° C.: | 83 | 90 | 92.5 | 105 | 115 | 410 | 225 | — |

Figure 3:
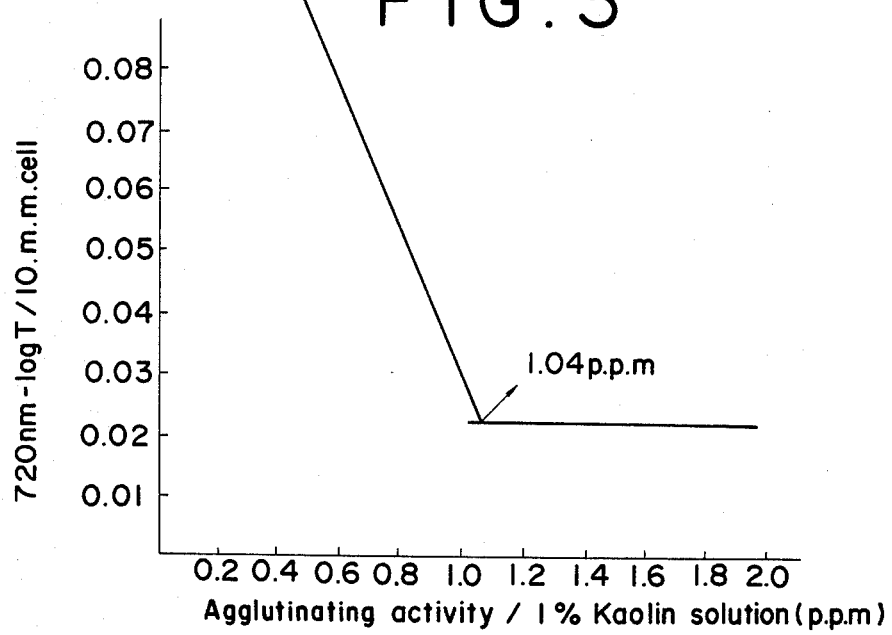
FIG. 3 is a graph showing the kaolin aggregative activity of the invented polysaccharide and a method for measuring the titer thereof.

(c) Aggregating Property:

The culture liquid or its aqueous solution of the present substance shows salient aggregating activity on a kaolin solution. Further, it quantitatively reacts with aluminum ion to instantaneously form a unique fibrous floc. Further, addition of an aqueous solution containing the present substance to an aqueous solution containing aluminum ion causes the solution to instantaneously gelatinize into a devil's tongue like state and to no longer show the aggregating activity without forming the fibrous floc. Further, mixing the present substance with synthetic high molecular cation causes it to form a strong floc. Meanwhile, the substance freely mixes with high molecular synthetic anion. This indicates that the substance has a property that is something like an anion aggregating agent. FIG. 3 shows the results of aggregating reaction tests conducted by using the present substance together with a kaolin solution. This serves as a yard-stick for measuring the aggregating titer in a solution during the culturing manufacture of the present substance. This permits accurate and quick measurement in microunit (ppm) and is an analysing method established by the present inventors. Further, this analysing method was used for screening the fungus produced by the present substance.

The tests the results of which are as shown in FIG. 3 were conducted under the following conditions: A 1% kaolin solution was stirred. After stirring, it was left intact for five minutes. The pH value was 3.5. The tests were conducted at room temperature. The test results shown in FIG. 3 indicate that one mg of the present substance is capable of completely aggregating and precipitating in five minutes that 1% kaolin solution which corresponds to 10 g of kaolin.

Aggregation Test (1)

Figure 4:
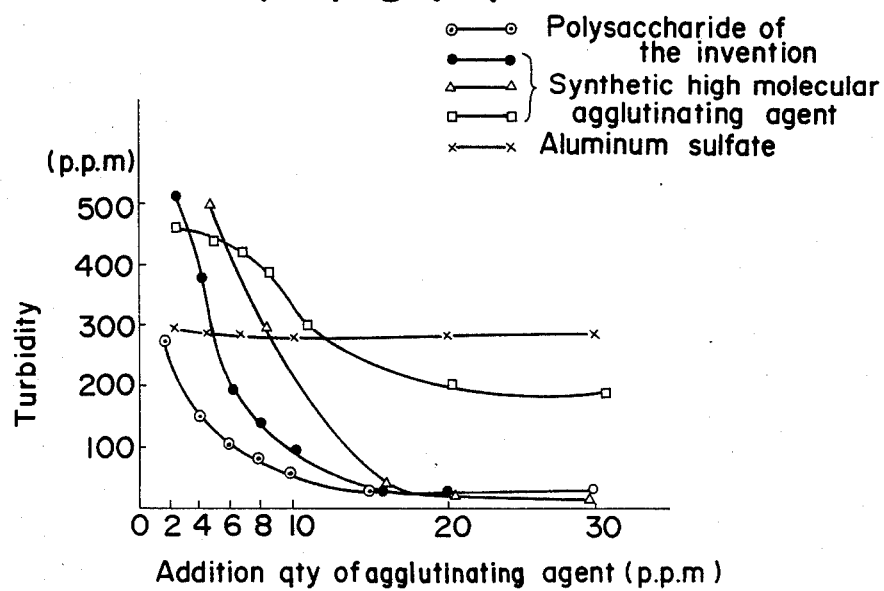
FIG. 4 is a graph showing the results of comparison of the agglutinating activity of the invented polysaccharide with that of a synthetic high molecular aggregation agent with a 5% kaolin solution used.

Using 5% kaolin solution as sample for aggregation tests, 400 ml of the kaolin solution was put in a 500 ml beaker. Each test was conducted using a jar and a tester. The reaction for measurement was carried out under the following conditions: The pH value was 4.6. Stirring was carried out at 30 rpm/min. The temperature was room temperature. Each aggregating agent was used in the form of a 1,000 ppm aqueous solution. The test results were as shown in FIG. 4. As shown, the floc produced by the present substance was fibrous and had high precipitating velocity. Compared with the conventional synthetic high molecular aggregating agent, the aggregating power of the substance was stronger by several times.

Table 6 shows the results of tests which were conducted to find the reactivity of the present substance with Al$^{+++}$. Aluminum sulfate was used as Al. Aluminum ion was added in the ratios as shown in Table 6. With aluminum ion added, stirring was carried out. After stirring, a centrifugation treatment was carried out at 5,000 rpm for 10 minutes. A precipitate thus obtained was washed with water and ethanol, dried under reduced pressure, and weighed to obtain the ratio thereof to the added aluminum.

TABLE 6

| Invented polysaccharide 100 mg/100 ml | $Al^{+++}$/invented polysaccharide, ratio by weight | Weight of aggregated polysaccharide by $Al^{+++}$ | Residual aggregating activity |
|---|---|---|---|
| Qty of added aluminum: | | | |
| 1 mg | 1/100 | 40 mg | + |
| 2 | 1/50 | 80 | + |
| 2.5 | 1/40 | 100 | − |
| 3 | 1/30 | 103 | − |
| 4 | 1/25 | 104 | − |
| 5 | 1/20 | 105 | − |

When the ratio by weight of Al to the polysaccharide of the present invention is not exceeding 1:40, the present substance becomes completely insoluble. However, when the ratio is 1:50, 20% of the substance remains not aggregated. It will be understood from Table 6 that the reaction ratio of Al to the present substance is 1:40. In other words, the addition of Al to the aqueous solution of the present substance in the ratio by weight of 1/40 to the substance causes the latter to be completely aggregated to become insoluble.

Figure 5:
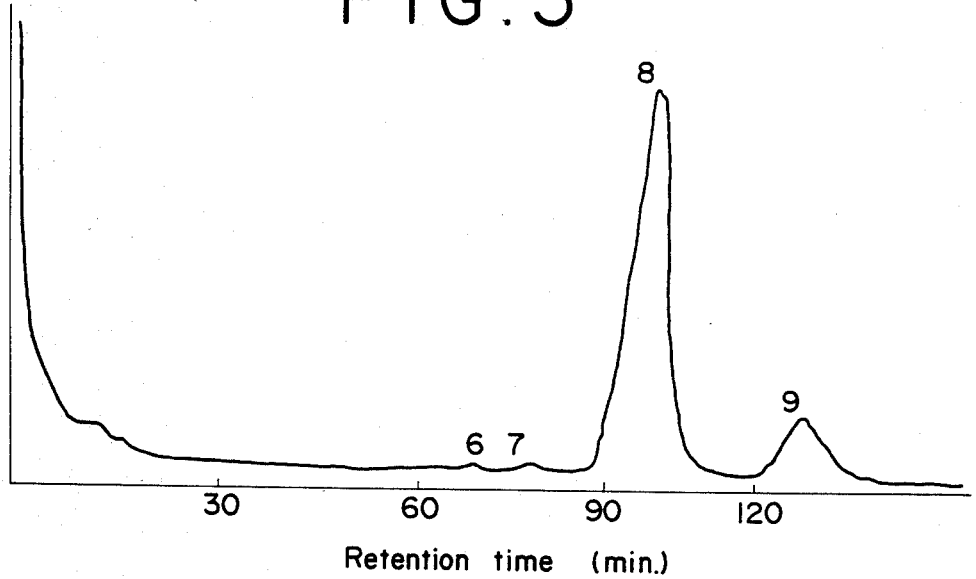
FIG. 5 is a gas chromatogram showing the results of alditol acetate analysis of a completely hydrolyzed product obtained from the invented polysaccharide. A peak 9 represents inositol which is an internal standard. The main constituent of the polysaccharide of the invention is represented by a peak 8. There are also very small peaks including a peak 6 representing mannose and another peak 7 representing galactose. The measuring conditions of the gas chromatogram were as follows: $H_2$ was used as carrier gas at a flow rate of 180 ml/min. The column used measured 2.1 m (L)×3 mm (dia.). The packing: ECNSS-M 5%; support "Chromosorb-W"; 60/80 mesh; and temperature was 170° C.

IV. Structural Feature:

(a) The constitutive Monosaccharide of the Present Substance:

Using an egg-plant type flask of 50 ml, 10 mg of a sample was put in the flask. To this was added 0.5 ml of 72% sulfuric acid with stirring carried out over a period of 30 min at 30° C. to make it soluble thereby. Then, 4 ml of water was added to the solubilized sample. Hydrolysis was carried out at 110° C. over a period of three hours. The hydrolyzate was neutralized with barium carbonate. Then, barium sulfate was removed by centrifugation. A supernatant thus obtained was condensed under reduced pressure to 5 ml. To this was added 30 mg of sodium boron hydride. This was then left intact at room temperature for four hours to have it reduced to alditol. An excess of sodium boron hydride was decomposed by adding 5% of acetic acid. The sample was dried under reduced pressure and then was acetylated with 1 ml of pyridine and 1 ml of acetic anhydride added at 110° C. over a period of three hours. Upon completion of the acetylation, 10 ml of water was added and drying was carried out under reduced pressure. An excess of the acetylation reagents was removed by repeating the above stated process three times. The sample thus processed was dissolved in chloroform and was subjected to measurement by gas chromatography. The results of measurement indicated that the sample comprised 90 to 95% of sugar. The glucide consisted at least 98% of glucose and less than 2% of mannose and galactose in total. The present polysaccharide contained 5% of galactose and mannose in total when it was of low purity. However, when it was purified to a higher purity, it came to show only the traces of galactose and mannose. The results of measurement were as shown in the gas chromatogram of FIG. 5.

Further, a 0.1 aqueous solution of the present substance was hydrolyzed with 1N and $H_2SO_4$ at 100° C. over a period of 5 hours, neutralized by an ordinary method and condensed. After that, the substance was examined by paper chromatography for the constituent sugar thereof. As a result of this, only glucose was detected there.

The paper chromatography developer: Butanol, pyridine and water in the ratio of 6:4:3. Development: 25 cm, twice. The color former used: A.H.P. In cases where the present substance was of low purity, traces of galactose and mannose were detected.

Figure 6:
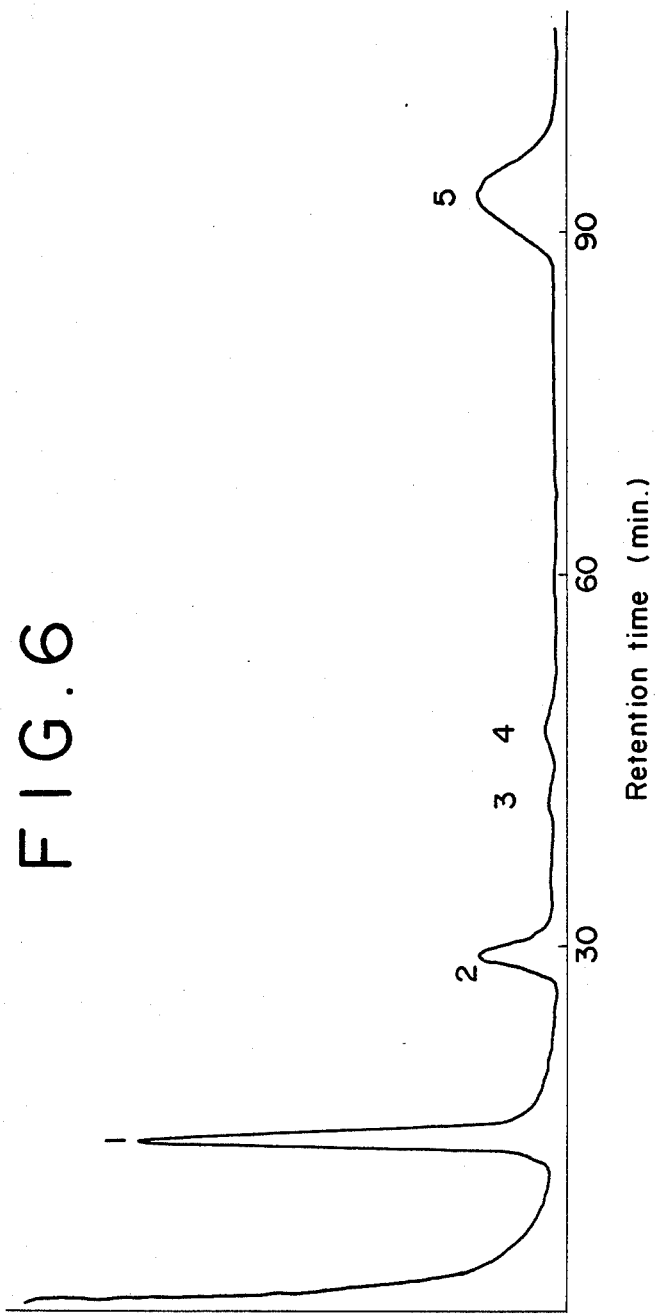
FIG. 6 is a gas chromatogram showing the results of methylated alditol acetate analysis of the invented polysaccharide. In this gas chromatogram, peaks 1, 2, 3, 4 and 5 respectively represent 2, 3, 4, 6-O-Me-G, 2,4,6-O-Me-G, 2,3,4-O-Me-G, 2,3,6-O-Me-G, and 2,4-O-Me-G. $N_2$ was used as carrier gas at a flow rate of 30 ml/min. The column measured 2.1 m×3 mm. The packing: 0.3% OV-275+0.4% GEXF 1150; support "Shimalite-W; 80/100 mesh; and temperature was 140° C.

(b) Bonding Mode of Sugar:

The determination of the bonding mode of sugar was carried out by methylation in accordance with the Hakomori's method. First, 50 mg of a sample was added to 10 ml of dimethyl sulfoxide and dissolved with stirring carried out at 60° C. over a period of one hour. A solution thus obtained was kept at temperature between 20° and 30° C. under a nitrogen gas stream with stirring. To this was added 2 ml of methyl sulfinyl carbanion. A reaction was allowed to proceed for three hours. Upon completion of the reaction, 1 ml of methyl iodide was added. A further reaction was allowed to proceed for one hour to complete a methylation process. The reaction liquid was subjected to dialysis which was carried out with flowing water overnight. The liquid within the dialysis membrane was extracted with chloroform. The chloroform layer thus obtained was dried under reduced pressure to obtain a methylated polysaccharide. The methylated polysaccharide thus obtained was subjected to measurement by infrared absorption spectrum. Methylation was confirmed by disappearance of an OH absorption at 3400 $cm^{-1}$. In cases where the methylation was not sufficiently effected, methylation was again carried out by repeating the same process. The methylated sugar thus obtained was made into alditol acetate and was analysed by gas chromatography (GLC) and a mass spectrometer (Mass) to identify peaks. The mole ratio was obtained from the areas of the peaks. The results of the above stated gas chromatography were as shown in FIG. 6. The results indicated: 2, 3, 4, 6-O.Me-G (O-methyl glucose) ($G^1\rightarrow$): 2, 4, 6-O-Me-G ($\rightarrow^3G^1\rightarrow$): 2, 4-O-Me.G ($\rightarrow^3G^1\rightarrow$)=3:1 to 2:3. Further, $G_6^1\rightarrow$ and $\rightarrow^4G^1\rightarrow$ were detected by this analysis, the content thereof was about 1%.

The bonding mode of the constituent sugar (glucose) as judged from the results of the analysis was of the following structure (I) or (II):

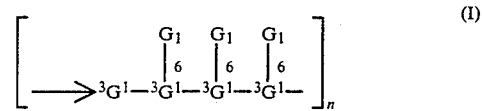

(I)

or

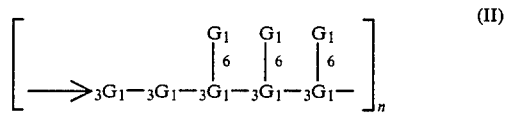

(II)

(c) $^{13}$C-NMR (carbon nuclear magnetic resonance) Spectrum:

The magnetic resonance absorption spectrum of the $^{13}$C nuclear was measured by using a Fourier's transformation type nuclear magnetic resonance absorption apparatus, Model Fx-60 manufactured by Nippon Denshi. The sample had been methylated in accordance with the Hakomori's method beforehand. The methylated sample was dissolved in heavy chloroform-$\alpha_1$ (CDCl₃) and tetramethyl silane (TMS) was used as internal standard. Measuring frequency was 15.1 MHz.

Figure 8:
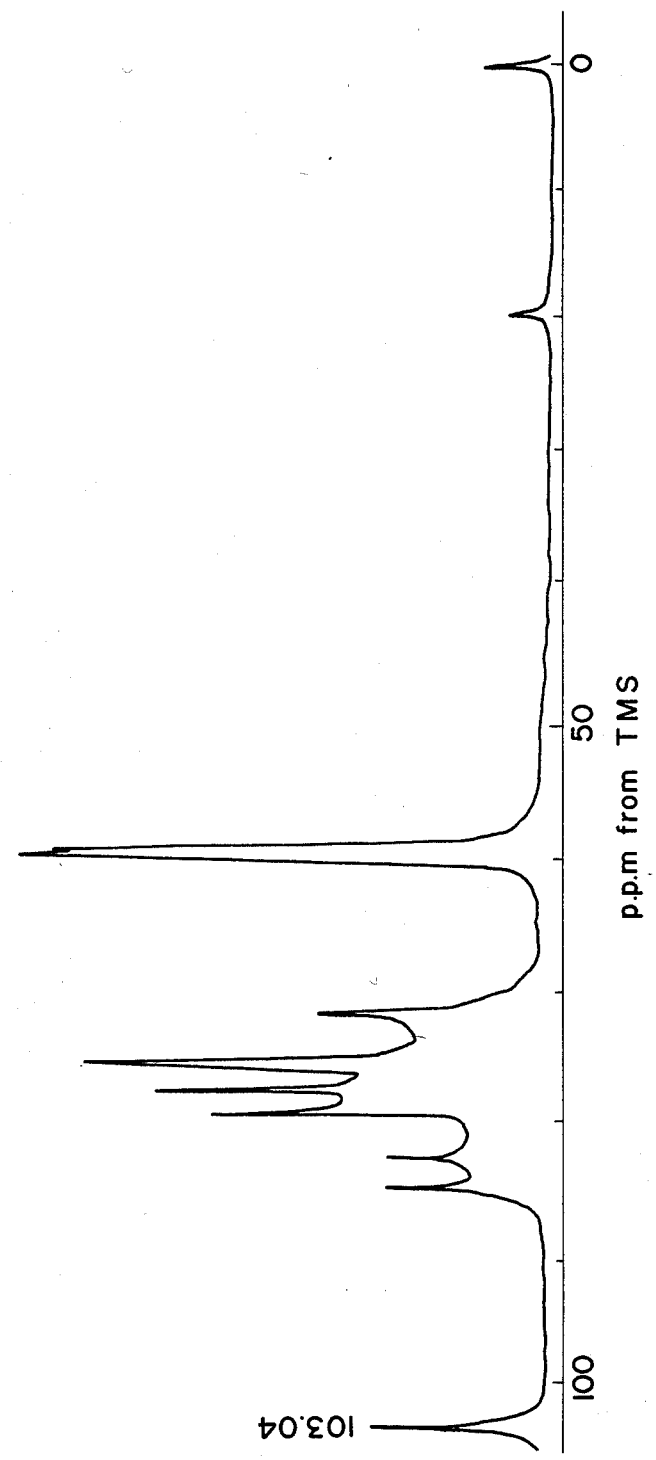
FIG. 8 shows $^{13}$C-NMR of a heavy chloroform solution of a methylated polysaccharide of the invention.

The results of this were as shown in FIG. 8. In this drawing, the absorption in the area of 60 to 80 ppm represents an overlap of an absorption by the carbon of a 2 to 6 methoxyl group of a pyranose ring and a triplet (75.1, 77.2 and 79.2 ppm) of the heavy chloroform. An absorption which is clearly observable around 103 ppm is due to β-anomeric glycoside bond. Further, since there is seen no absorption due to α-anomer around 90 to 100 ppm, it will be understood that both the (1–16) linkage and (1–3) linkage are β-oriented in the present substance.

Figure 9:
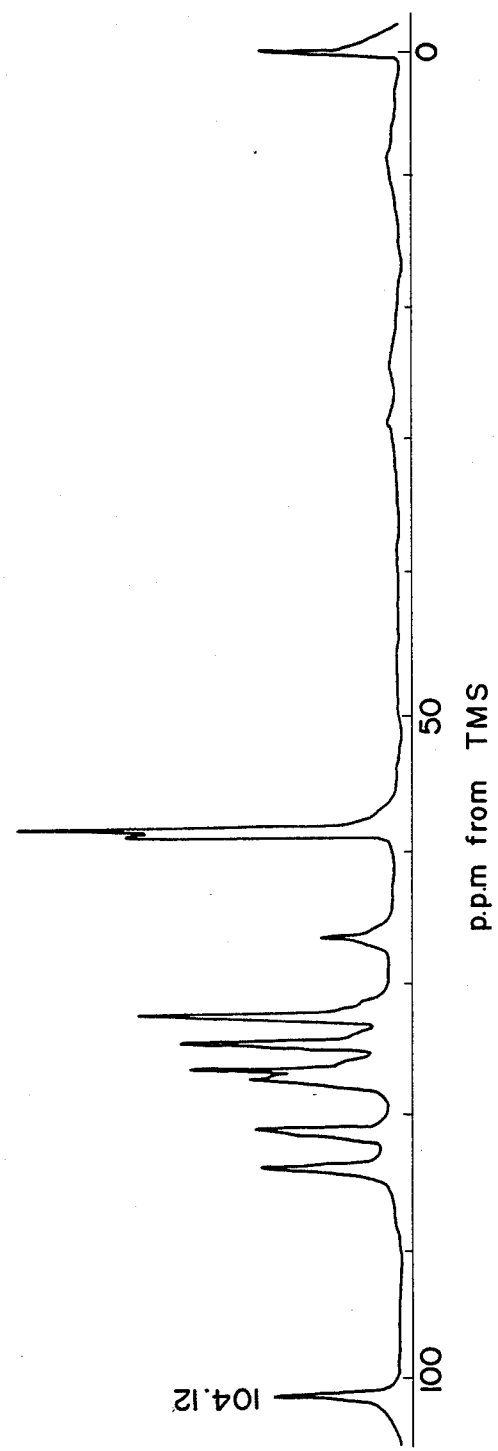
FIGS. 9 and 10 show, for the purpose of comparison, $^{13}$C-NMR of matters obtained by methylated pustran of β-anomer and methylated dextran of lanomer.
Figure 10:
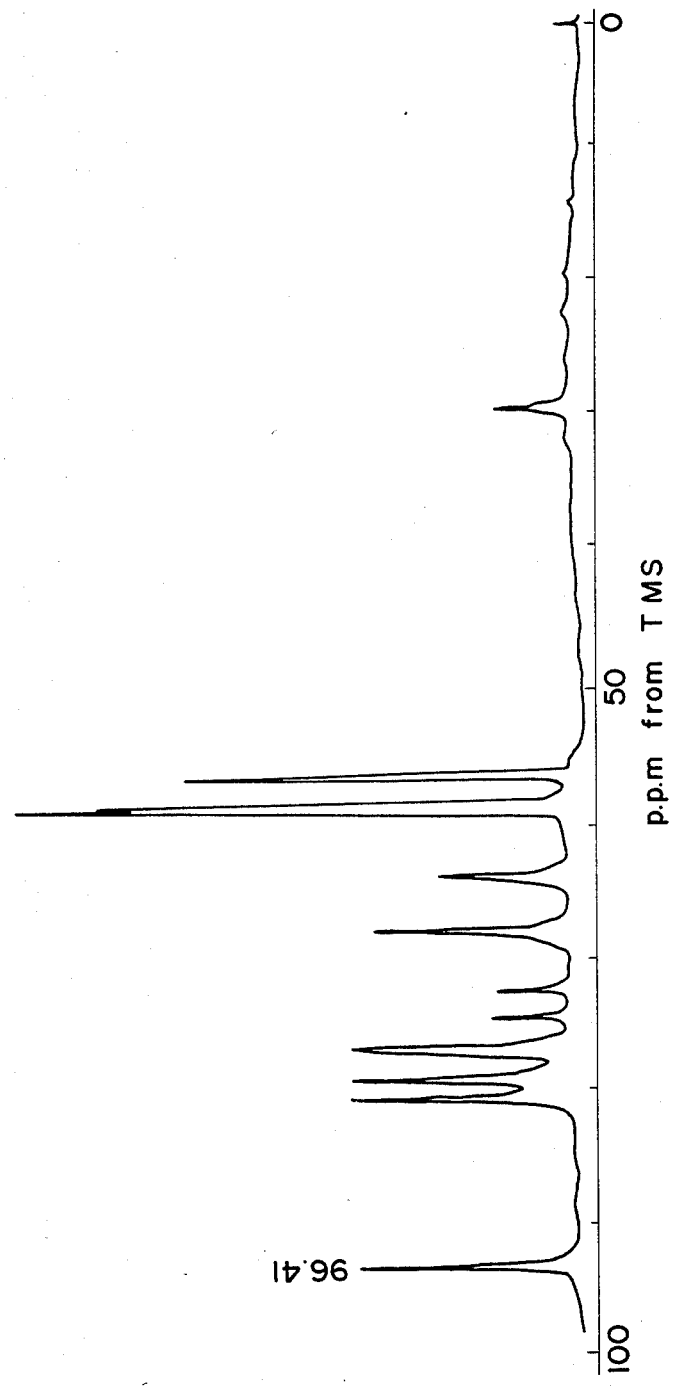

For the sake of comparison, FIGS. 9 and 10 show β-anomer methylated psutulan and α-anomer methylated dextran.

Figure 7:
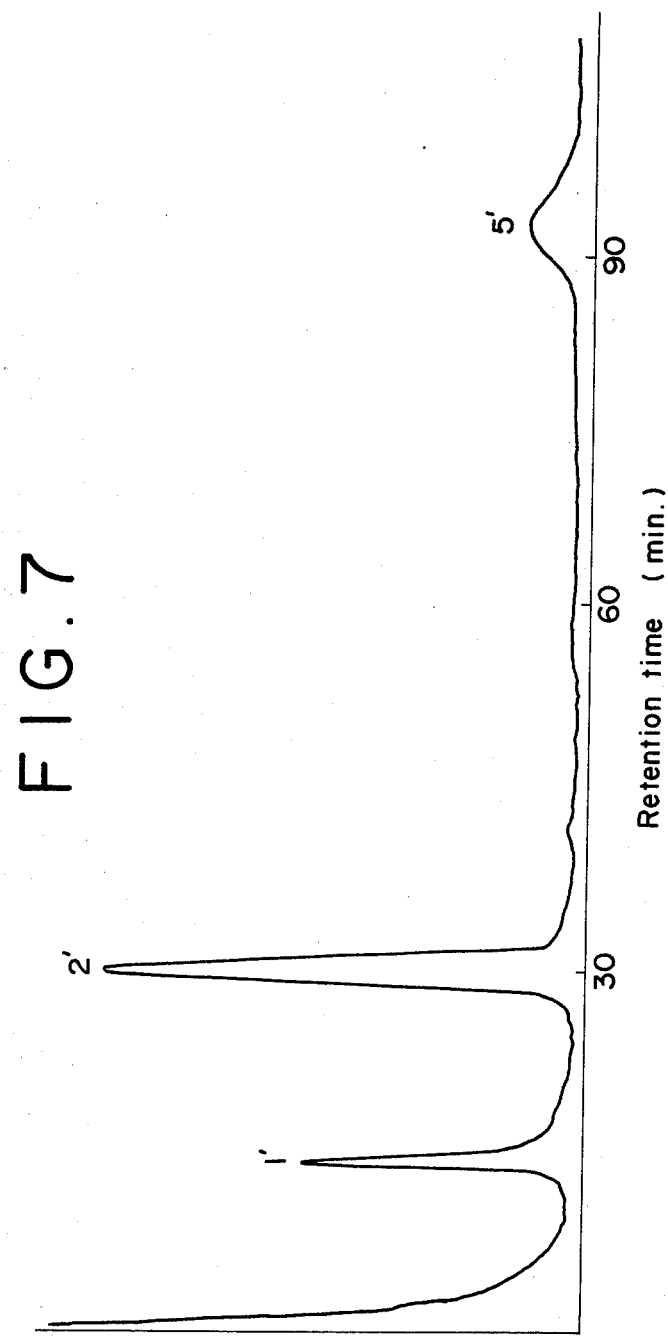
FIG. 7 is a gas chromatogram showing the results of methylated alditol acetate analysis of a nondecomposed polysaccharide obtained through partial hydrolysis of the invented polysaccharide carried out with 1N-sufuric acid over 5 hours. Compared with FIG. 6, the peaks 1 and 5 decreased while the peak 2 increased. This indicates the liberation of the non-reducing end-group. The measurement conditions of the gas chromatogram were the same as those of FIG. 6.

(d) Acid or Enzyme Decomposition:

Hydrolysis at 100° C. of the present substance with 1N (mineral acid, HCl, H₂SO₄) brings about complete aggregation of an insoluble matter. The insoluble matter obtained by hydrolysis in this manner was isolated and examined by an ordinary known method for the constituent sugar and bonding mode thereof. The constituent sugar included glucose only. As for the bonding mode, the insoluble matter was mainly composed of →¹G³→ while G¹→ disappeared almost completely. In other words, the non-reducing end-group had been reduced to a great extent. This indicates that 1,6 bond was preferentially decomposed. A gas chromatogram of this is as shown in FIG. 7.

As mentioned in the foregoing, it is apparent from the ¹³C nuclear magnetic resonance spectrum or from the results of GC and MS analysis that the present substance has β-1,3-linkage as principal chain; has the non-reducing end-group branching in β-1,6-linkage and is a β,1,3 glucan containing 38% to 43% of the non-reducing end-group therein. In the meantime, the present inventors has also examined an enzyme action on the present substance in the following manner: An exo,-type 1,3βglucangluco hydrase (an enzyme which decomposes the β,1,3 bonds of glucose from the non-reducing end-group one after another for example, from laminarin solely consisting of the β,1,3 linkage of glucose), a product of Sigma Co. isolated from bacidiomycetes, and known by the trade name of "Lysing-Enzyme, was allowed to act on the present substance. The substance thus processed was examined for decomposed sugar by paper chromatography to detect therein glucose, gentiobiose (which is a disaccharide having glucose bonded in β, 1, 6) and glucose-6-phosphate. The rate of decomposition of the substrate did not exceed 1% as reduced to glucose. The very low rate of decomposition of the invented polysaccharide by the above stated enzyme seems to be attributable to the following reasons: (1) Because of the physical structure of this substance. In an aqueous solution, this substance, microscopically, forms a gel and, since this deprives the enzyme of affinity for the substrate, it is only a solubilized portion of the surface polysaccharide that is decomposed. (2) The enzyme might be blocked by the phosphoric acid group contained in this substance or by an acid matter liberated by alkalinity. As for the latter of the conceivable reasons, however, examination of the rate of decomposition of this substance by enzyme after removal of the acid matter with alkali did not reveal any change. Further, phosphatase was allowed to act on this substance to remove 30 to 40% of phosphoric acid and then the rate of decomposition by the enzyme was also examined. Although the rate somewhat increased (at least by 1%) in this case, the decomposition rate was still low. Meanwhile, the relative viscosity of the aqueous solution did not show much change after the enzyme was allowed to act thereon. The viscosity was lowered when a culture liquid of bacteria newly screened by using the polysaccharide of the present invention as carbon source (a culture liquid after removal of fungus body) was added to this substance with phosphatase further added and was thus allowed to act thereon with slight alkali (pH 8.3). Then, the rate of decomposition of this substance became several ten percent. The decomposition liquid thus obtained contained glucose, gentiobiose, oligo-saccharide and glucose-6-phosphate which were tri- and tetra-saccharides and a polysaccharide which was precipitated by 50% ethanol.

Judging also from the color forming spots of glucose and gentiobiose detected by paper, gentiobiose was in greater quantity than glucose. The enzymes contained in this culture liquid are believed to include Exo-β1,3-glucanase because there were produced glucose and gentiobiose and also include endo-β1,3-glucanase because the viscosity was lowered and there was produced a polysaccharide that was precipitated by 50% ethanol. In addition to them, it is also believed that the culture liquid further included an enzyme that macroscopically decompose this substance in a unique manner. Anyway, in the polysaccharide of the present invention, there were produced exo-β1,3 glucanase, expβ1,3 glucanase and phosphatase and also, by the combination of phosphatase with the culture liquid of newly isolated bacteria, etc., gentiobiose, glucose-6-phosphate and glucose. Therefore, the skeletal structure of the invented polysaccharide (the bonding mode of the constituent glucose) obtained from chemical and physical analyses coincides with the findings obtained from the examination of enzymatic decomposition. In other words, the invented polysaccharide is believed to be a high molecular polysaccharide having such a skeletal structure that the principal chain is formed by β1,3, linkage of glucose while the non-reducing end-group thereof branches in β,1,6 linkage and that a portion of phosphoric acid is ester bonded in the polysaccharide in the form of glucose-6-phosphate.

EXAMPLE OF ENZYMATIC DECOMPOSITION

The purified powder of the polysaccharide of this invention was dissolved in distilled water to obtain a 0.1% solution thereof. This was used as substrate. The working enzyme was selected from the following: The exo 1,3,-β glucanase employed was an enzyme called by the trade name of "Lysing Enzyme, which was manufactured by Sigma Co. and isolated from basidiomycetes. The phosphatase employed was alkali or acid phosphatase or phosphodiesterase, etc. manufactured by P.L.-Biochemical Co. As for the newly isolated fungus, the culture liquid thereof was directly used. (The culture liquid was prepared in the following manner: 0.1% of the novel polysaccharide was used as carbon source; N 0.1%; pH 8.3; culture temperature 35° C.; and fungus body was removed at 10,000 rpm.) The working conditions were as follows: Lysing Enzyme-temperature was 50° C. pH was 5.0 10 mg/20 ml of the enzyme was added to the substrate in the ratio of 1 ml/250 ml. (This enzyme bypasses the side chain of the 1,6,β bond.) The working conditions of the alkali or acid phosphatase were as follows: The temperature was 35° C.; pH was 5.2 or 8.2. The addition quantity of each enzyme was 0.02 ml (1 mg/1 ml). Working time: 72 hrs. The decomposition liquid was processed with 50% ethanol to remove insoluble matter therefrom and was condensed. After that, development was effected with butanol:-pyridine:water=6:4:3:50 cm (25 cm, twice). Color forming: By A.H.P.

The results were as shown in Table 7.

TABLE 7

|   | Working time | Rate of decompos'n | Relative viscosity/20° C. (ratio, assuming nontreated liquid to be 100 | Decomposed sugar detected by paper chromatography |
|---|---|---|---|---|
| (1) Exo, 1,3 glucanase (Lysing Enzyme) | 72 | 1% or less | 95–99 | Glucose Gentiobiose Glucose-6-phosphoric acid |
| (2) Alkali phosphatase (Lysing Enzyme) | 72 | 1% or less | 90–95 | Glucose Gentiobiose Glucose-6-phosphoric acid |
| (3) Alkali phosphatase, cultured liquid of newly isolated fungus (bacteria) | 72 | 20 to 30% | Not exceeding 10 | Glucose Gentiobiose Tri-, tetra-saccharide (oligo-saccharide) Polysaccharide, precipitated by 50% alcohol |

(e) Phosphoric Acid in the Invented Polysaccharide:

The total phosphorus content of the invented polysaccharide was colorimetrically determined in accordance with the Allen's improved method or with the Deniges-Atkins method after carbonic acid melting. As a result of this, it became apparent that the polysaccharide of the invention contained 4 to 6% of phosphoric acid ($PO_4$). Meanwhile, results of fluorescent X-ray analysis and enzymatic decomposition also clearly showed that phosphoric acid ($PO_4$) was contained therein. With regard to phosphoric acid containing high molecular polysaccharides in general, there have been reports on mannan, galactan, etc. However, with the exception of starch (the phosphoric acid content of polysaccharide starch is less than 0.1%), there has been no report on $\alpha$-$\beta$ glucan. The phosphoric acid content of the invented polysaccharide does not vary with the degree of purification. It, however, somewhat varies with culture conditions.

When the novel polysaccharide is hydrolyzed with 1N HCl at 100° C., phosphoric acid is liberated therefrom. With the polysaccharide further hydrolyzed, the polysaccharide which was thus rendered insoluble was examined for phosphoric acid contained therein. Then, it was found that the phosphoric acid content became a trace. When the invented polysaccharide was alkali treated with 1N NaOH at 100° C. for a period between 10 and 30 minutes, the phosphoric acid remained unaltered by the treatment.

Further, when a 0.1% aqueous solution of the polysaccharide of the invention was treated with acid or alkali phosphatase or phosphodiesterase or the like, the phosphoric acid was liberated. However, the maximum rate of decomposition of the liberated phosphoric acid was 50% of the total phosphorus contained in the polysaccharide. This decomposition rate hardly exceeded 50% even when exo $\beta$-1,3 glucanase was used in combination with this enzyme. Such a limit to the decomposition rate is judged to be attributable to the physical structure of the polysaccharide of the invention. There was contained no phosphoric acid in the methylated polysaccharide. When the polysaccharide was treated with exo-$\beta$,1,3 glucanase, glucose-6-phosphate was detected by paper chromatography out of the portion decomposed by this enzyme. This indicates that a portion of the phosphoric acid contained in the polysaccharide of the invention becomes glucose-6-phosphate acid.

Figure 11:
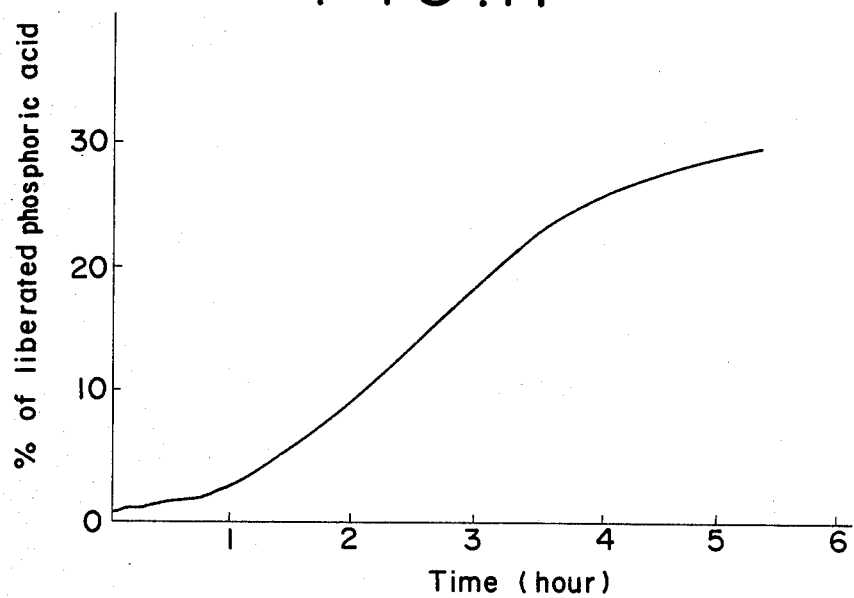
FIG. 11 is a graph showing the ratio of liberated phosphoric acid liberated by phosphatase alkaline to total phosphoric acid in relation to the lapse of time.

Further, the presence of diester bonded phosphoric acid is also conceivable. The mole ratio of the phosphoric acid content to the main constitutive sugar (glucose), phosphoric acid ($PO_4$): glucose, is 1:8–12. FIG. 11 shows the rate of phosphoric acid liberation by phosphatase in the 0.1% aqueous solution of the polysaccharide of the invention. The results of analysis conducted in this connection were as shown in Table 8 below:

TABLE 8

| Test sample | Content, Deniges-Atkins method after carbonic acid melting | Alkali or acid phosphatase treat't Content | Alkali or acid phosphatase treat't Rate of liberation | Content, fluorescent X-ray method |
|---|---|---|---|---|
| Novel polysaccharide (purified) | 4–6% | 2–3% | 50% | +++ |
| No Sevag, no dialysis (not purified) | 4–6% | 2–3% | 50% | +++ |
| Acid hydrolysis residue | Trace | Trace |  | ± |
| Alkali treated | 4–6% | 2–3% | 50% | +++ |
| Methylated polysaccharide | — | — |  | — |

It is apparent from the foregoing that phosphoric acid is contained in the polysaccharide of the invention in a state of being bonded with sugar. It is one of the features of this substance that phosphoric acid is contained in a great degree in $\beta$,1,3 glucan.

V. Subacute Toxicity:

The polysaccharide of the invention was subjected to tests for acute and subacute toxicity thereof. The test results were as described below:

Animals used for tests: Mature male and female Wister rats, 13 week old.

Test method: Each group consists of 10 male and 10 female rats. The polysaccharide of the invention was used in quantity 25 mg/kg BW/day for Group A and 2.5 mg/kg BW/day for Group B. Oral dosing was carried out with a tube over a period of 7 weeks. Meanwhile, city water was given to a control group. Measurement of body weight and observation of health condition were carried out at the time of oral dosing. Blood letting was carried out before the start and immediately before the end of tests to measure the hematocrit value, number of red blood corpuscles, number of white blood corpuscles and the demarcation ratio of the white blood corpuscles. After completion of the oral dose period (8th week), the blood of each rat was discharged under narcosis. Then, main organs were pathologically and histologically examined together with observation with the unaided dye.

Test Results and Comments (1) Change in Body Weight: During the dosing period, each group did not show much change in their growth curve. Each group did not show any significant difference between their body weight before the start of test and their body weight at the end of the test. No tangible changes were observed in their health during the dose period.

(2) Comments on Matters relative to Blood: No changes were seen in all values.

(3) Pathological Comments: Both the observation with the unaided eye and observation made pathologically and histologically did not reveal much changes.

As apparent from the foregoing, the polysaccharide of the present invention is useful as an aggregating agent, a food modifying agent and a medicine for intestine conditioning and other medical purposes. Other connceivable applications of the present invention include: Jam, marmalade, mayonnaise, salad dressing, ketchup, juices, soup, sauce, soy, bean jam, jelly, ice-cream, yoghurt, coffee-milk, chocolate, beer, refined sake, foreign liquors, sausage, ham, tubular shaped fish paste, vermicelli, boiled fish paste, instant servable foods and edible covering film for food products, etc. Further conceivable applications include medicinal uses such as a blood plasma substitute, an anticoagulant for blood, a cornea medicine and an antitumor substance; an additive for cosmetics; size for the paper making industry; a lubricant for the textile industry and oil well boring; an auxiliary for freezing stabilization; a floatation liquid; an auxiliary for fire extinguishing liquid; a soil reforming agent; a tablet coating material; and other applications for architectural purposes, ceramics, etc.

What is claimed is:

1. A polysaccharide having D-glucose as main constitutive sugar therein as detected by gas chromatography carried out through methylation and hydrolysis and by paper chromatography carried out through acid hydrolysis in accordance with the Hakomori's method; showing

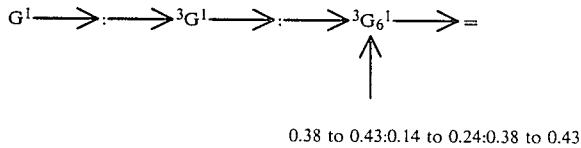

0.38 to 0.43:0.14 to 0.24:0.38 to 0.43 in gas chromatographic mass spectrometry (GC-MS method); having the absorption position of $C_1$ at 103 ppm as measured from a $^{13}C$-nuclear magnetic resonance spectrum; showing characteristic absorption at 1720 cm$^{-1}$–1760 cm$^{-1}$ and 890 cm$^{-1}$ in an infrared absorption spectrum; having number average molecular weight between 50,000 and 500,000 as measured by the osmotic method; having a specific rotation $[\alpha]_D^{25}$ between +20 and +70; consisting 42.0 to 45.0% of carbon, 5.7 to 6.7% of hydrogen, 0 to 1.0% of nitrogen, 0.2 to 0.8% of ash content and the rest of oxygen according to the results of an elementary analysis; containing 4.0 to 6.0% of phosphoric acid in total therein as measured by a fluorescent X-ray analysis, the Allen's improved method and the Deniges-Atkins method after carbonic acid melting showing a color reaction of saccharides in an α-naphthol-sulfuric acid reaction, an indole-sulfuric acid reaction and a phenol-sulfuric acid reaction; being negative in a ninhydrin reaction, a carbazole-sulfuric acid reaction and an Elson-Morgan's reaction; being soluble in dimethyl sulfoxide (DMSO); swelling well in water though not readily soluble therein; and being insoluble in ethanol, pyridine, chloroform and other organic solvents.

2. A polysaccharide according to claim 1, characterized in that, when hydrolysis is carried out thereon with 1N-acid (mineral acid) at 100° C. for three hours, the polysaccharide has $G^1 \rightarrow$(non-reducing end-group) thereof decomposed and liberated to produce an insoluble polysaccharide which has $\rightarrow ^3G^1 \rightarrow$ mainly linked therein; with an alkali treatment carried out thereon at pH 10.0, at 100° C., for 10 minutes, infrared absorption at 1720 cm$^{-1}$–1760 cm$^{-1}$ disappears; the polysaccharide is not decomposed at all by isoamylase and pullulanase; although the polysaccharide is caused to produce glucose, gentiobiose and glucose-6-P acid by the action of exo-β,1,3-glucanase, the hydrolyzing rate thereof is about 1%; and the polysaccharide is caused to liberate phosphoric acid by alkali or acid phosphatase and also by phosphodiesterase, the ratio of this liberation to total phosphorus not exceeding 50%.

3. A polysaccharide according to claim 1 or 2, wherein the structure of said D-glucose which is the main constitutive sugar is such that: the principal chain is composed of β,1,3-G linkage the non-reducing end-group thereof branches in β,1,6-G linkage said non-reducing end-group amounting to 38.0 to 43.0%; there is contained 4 to 6% of phosphoric acid; and the polysaccharide liberates acid matters when subjected to an alkali treatment.

4. A polysaccharide according to claim 1, 2 or 3, which is gelated by strong acid or strong alkali, the gel thus formed separating from water when left intact; has the viscosity thereof increased and thus comes to take a jelly like form when mixed with an aqueous solution of glucose, fructose or sucrose; when the concentration thereof is not exceeding 80%, the viscosity thereof increases with the concentration and thus comes to take a jelly like form; the aqueous solution thereof has no adhesiveness; is highly emulsifiable; has a slight degree of acidity; aggregates kaolin from a kaolin solution, 1 mg of the polysaccharide being capable of completely aggregating and precipitating a 1% kaolin solution (containing 10 g kaolin) in 5 minutes; insolubilizes a basic protein or some specific enzymes; brings about an aggregating reaction with aluminum to form a fibrous floc; in a pure aqueous solution system, reacts quantitatively; also forms an insoluble floc with bi- or trivalent inorganic ion or heavy metal other than Al$^{+++}$ in the ratio by weight of 1:1/40 thereof; and shows properties similar to those of a synthetic high molecular anion aggregating agent.

5. An aggregating agent comprising a polysaccharide having D-glucose as main constitutive sugar therein as detected by gas chromatography carried out through methylation and hydrolysis and by paper chromatography carried out through acid hydrolysis in accordance with the Hakomori's method; showing

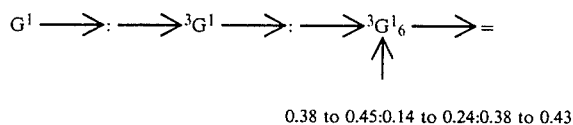

0.38 to 0.45:0.14 to 0.24:0.38 to 0.43 in gas chromatographic mass spectrometry (GC-MS method); having the absorption position of $C_1$ at 103 ppm as measured from a $^{13}C$-nuclear magnetic resonance spectrum; showing characteristic absorption at 1720 cm$^{-1}$–1760 cm$^{-1}$ and 890 cm$^{-1}$ in an infrared absorption spectrum; having number average molecular weight between 50,000 and 500,000 as measured by the osmotic method; having a specific rotation $[\alpha]_D^{25}$ between +20 and +70; consisting 42.0 to 45.0% of carbon, 5.7 to 6.7% of hydrogen, 0 to 1.0% of nitrogen, 0.2 to 0.8% of ash content and the rest of oxygen according to the results of an elementary analysis; containing 4.0 to 6.0% of total phosphoric acid in total therein as measured by a fluorescent X-ray analysis, the Allen's improved method and the Deniges-Atkins method after carbonic acid melting; showing a color reaction of saccharides in an α-naphthol-sulfuric acid reaction, and indole-sulfuric acid reaction and a phenol-sulfuric acid reaction; being negative in a ninhydrin reaction, a carbazole-sulfuric acid reaction and Elson-Morgan's reaction; being soluble in dimethyl sulfoxide (DMSO); swelling well in water though not readily soluble therein; and being insoluble in ethanol, pyridine, chloroform and other organic solvents.

6. A food modifier comprising a polysaccharide which has D-glucose as main constitutive sugar therein as detected by gas chromatography carried out through methylation and hydrolysis and by paper chromatography carried out through acid hydrolysis in accordance with the Hakomori's method; shows

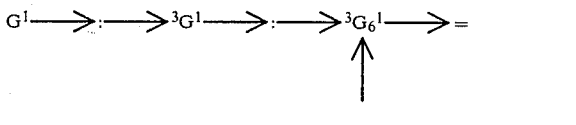

0.38 to 0.43:0.14 to 0.24:0.38 to 0.43 in gas chromatographic mass spectrometry (GC-MS method); has the absorption position of $C_1$ at 103 ppm as measured from a $^{13}C$-nuclear magnetic resonance absorption spectrum; shows characteristic absorption at 1720 cm$^{-1}$–1760 cm$^{-1}$ and 890 cm$^{-1}$ in an infrared absorption spectrum; has number average molecular weight between 50,000 and 500,000 as measured by the osmotic method; has a specific rotation $[\alpha]_D^{25}$ between +20 and +70; consists 42.0 to 45.0% of carbon, 5.7 to 6.7% of hydrogen, 0 to 1.0% of nitrogen, 0.2 to 0.8% of ash content and the rest of oxygen according to the results of an elementary analysis; contains 4.0 l to 6.0% of phosphoric acid in total therein as measured by a fluorescent X-ray analysis, the Allen's improved method and the Deniges-Atkins method after carbonic acid melting; shows a color reaction of saccharides in an α-naphthol-sulfuric acid reaction, an indole-sulfuric acid reaction and a phenol-sulfuric acid reaction; is negative in a ninhydrin reaction, a carbazole-sulfuric acid reaction and an Elson-Morgan's reaction; is soluble in dimethyl sulfoxide (DMSO); swells well in water though not readily soluble therein; and is insoluble in ethanol, pyridine, chloroform and other organic solvents.

7. An analytical and research reagent comprising a polysaccharide which has D-glucose as main constitutive sugar therein as detected by gas chromatography carried out through methylation and hydrolysis and by paper chromatography carried out through acid hydrolysis in accordance with the Hakomori's method; shows

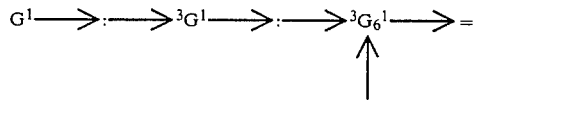

0.38 to 0.43:0.14 to 0.24:0.38 to 0.43 in gas chromatographic mass spectrometry (GC-MS method); has the absorption position of $C_1$ at 103 ppm as measured from a $^{13}C$-nuclear magnetic resonance spectrum; shows characteristic absorption at 1720 cm$^{-1}$–1760 cm$^{-1}$ and 890 cm$^{-1}$ in an infrared absorption spectrum; has number average molecular weight between 50,000 and 500,000 as measured by the osmotic method; has a specific rotation $[\alpha]_D^{25}$ between +20 and +70; consists 42.0 to 45.0% of carbon, 5.7 to 6.7% of hydrogen, 0 to 1.0% of nitrogen, 0.2 to 0.8% of ash content and the rest of oxygen according to the results of an elementary analysis; contains 4.0 to 6.0% of phosphoric acid in total therein as measured by a fluorescent X-ray analysis, the Allen's improved method and the Deniges-Atkins method after carbonic acid melting; shows a color reaction of saccharides in an α-naphthol-sulfuric acid reaction, an indole-sulfuric acid reaction and a phenol-sulfuric acid reaction; is negative in a ninhydrin reaction, a carbazole-sulfuric acid reaction and an Elson-Morgan's reaction; is soluble in dimethyl sulfoxide (DMSO); swells well in water though not readily soluble therein; and is insoluble in ethanol, pyridine, chloroform and other organic solvents.

* * * * *